United States Patent
Wei et al.

(10) Patent No.: US 6,482,655 B1
(45) Date of Patent: Nov. 19, 2002

(54) IMMUNOASSAY PROCEDURE UTILIZING FLUOROGENIC TRACER ANTIGENS

(75) Inventors: Ai-Ping Wei; James N. Herron, both of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 08/096,338

(22) Filed: Jul. 23, 1993

(51) Int. Cl.$^7$ .............................................. G01N 33/53
(52) U.S. Cl. ...................... 436/536; 436/537; 436/546; 436/172; 436/800; 436/805; 530/402
(58) Field of Search ................................ 436/536, 537, 436/546, 172, 800, 805; 530/402

(56) References Cited

U.S. PATENT DOCUMENTS

| | | | |
|---|---|---|---|
| 4,318,981 A | 3/1982 | Burd et al. | 435/7 |
| 4,975,380 A | 12/1990 | Hummelen et al. | 436/546 |
| 5,237,515 A | 8/1993 | Herron et al. | 364/498 |

FOREIGN PATENT DOCUMENTS

| GB | 2223096 | * | 3/1990 |
|---|---|---|---|

OTHER PUBLICATIONS

Jiskoot et al., "Preparation and Application of a Fluorescein–Labeled Peptide for Determining the Affinity Constant of a Monoclonal Antibody–Hapten Compex by Fluorescence Polarization", Analytical Biochemistry 196, pp. 421–426, 1991.

Kranz et al., "Kinetics and Mechanism of Deuterium Oxide–induced Fluorescence Enhancement of Ligand Bound to Specific Heterogeneous and Homogeneous Antibodies", The Journal of Biological vol. 256, No. 9, Issue of May 10, 4433–4438, 1961.

Ullman et al., "Fluorescent Excitation Transfer Immunoassay", The Journal of Biological Chemistry, vol. 251, No. 14, Issue of Jul. 25, pp. 4172–4178, 1976.

Barnard et al., "Chemical Sensors Based on Controlled–Release Polymer Systems", Science, vol. 25, pp. 927–929, Feb. 22, 1991.

Bates et al.. "Comparative Properties Of Monoclonal Antibodies Comprising A High–Affinity Anti–Fluorescyl Idiotype Family", Molecular Immunology, vol. 22, No. 8, pp. 871–877, 1985.

Bird et al., "Single–Chain Antigen–Binding Proteins", Science, vol. 242, pp. 423–426, Oct. 21, 1988.

Farkas et al., "Fluorescence properties of bichromophoric molecules", Spectrochimica, vol. 48A, No. 1, pp. 95–99, 1992.

Haas et al., "Distribution of End–to–End Distances of Oligopeptides in Solution as Estimated by Energy Transfer", Proc. Nat. Acad. Sci. USA, vol. 72, No. 5, pp. 1807–1811, May 1975.

Kranz et al., "Partical Elucidation Of An Anti–Hapten Repertoire In Balb/c Mice: Comparative Characterization Of Several Monoclonal Anti–Fluorescyl Antibodies", Molecular Immunology, vol. 18, No. 10, pp. 889–898, 1981.

Stryer et al., "Energy Transfer: A Spectroscopic Ruler", Biochemistry Proc. N.A.S., vol. 58, pp. 719–726, 1967.

Ullman et al., "Fluorescence Excitation Transfer Immunoassay (FETI)", Methods In Enzymology, vol. 74, pp. 28–60, 1981.

Wei et al., "Characterization of Fluorescent Dyes for Optical Immunosensors Based on Fluorescence Energy Transfer", Biosensor Design And Application, pp. 105–120, 1992.

Wenska G., "Bichromophoric Compounds As Chemical Models In The Study Of The Photochemistry Of Nucleic Acids", Journal of Photochemistry and Photobiology, A: Chemistry, 49, pp. 167–185, 1989.

* cited by examiner

Primary Examiner—Bao-Thuy L. Nguyen
(74) Attorney, Agent, or Firm—TraskBritt (57) ABSTRACT

Disclosed are fluorescent energy transfer dyes which are capable of moving between a more stacked configuration to exhibit fluorescent quenching and a more spaced configuration to exhibit fluorescence can be conjugated to a peptide epitope for use in the detection of an unknown antibody in bulk solution. The resulting labeled peptide reagent can be used in an immunoassay procedure by placing it in bulk solution along with the unknown antibody to be detected. When the antibody binds to the peptide epitope, the pair of dyes carried by the peptide epitope will have their configuration altered from a stacked to an unstacked configuration and will exhibit a fluorescent increase in response thereto.

11 Claims, 7 Drawing Sheets

NH-Gly-Ser-Gly-Ser-Arg-Leu-Pro-Gly-Pro-Ser-Asp-Thr-Cys

SEQUENCE LISTING (1) GENERAL INFORMATION:

(iii) NUMBER OF SEQUENCES:2

(2) INFORMATION FOR SEQ ID NO:1:

(i) SEQUENCE CHARACTERISTICS:
        (A) LENGTH:7 amino acids
        (B) TYPE:amino acid
        (D) TOPOLOGY:linear     (xi) SEQUENCE DESCRIPTION:SEQ ID NO:1:

Arg Leu Pro Gly Pro Ser Asp
1               5

(2) INFORMATION FOR SEQ ID NO:2:

(i) SEQUENCE CHARACTERISTICS:
        (A) LENGTH:13 amino acids
        (B) TYPE:amino acid
        (D) TOPOLOGY:linear     (xi) SEQUENCE DESCRIPTION:SEQ ID NO:2:

Gly Ser Gly Ser Arg Leu Pro Gly Pro Ser Asp Thr Cys
1               5                   10

IMMUNOASSAY PROCEDURE UTILIZING FLUOROGENIC TRACER ANTIGENS

BACKGROUND OF THE INVENTION

1. Technical Field

This invention relates generally to biological assays, and more specifically to assay reagents labeled with fluorescent materials which reagents can be "toggled" from an intramolecular dimer to a fluorescent monomer by antibody binding.

2. State of the Art

Most clinical assays (e.g., immunoassays, DNA probe assays) are heterogeneous and consist of at least two steps: the binding of an antigen to its antibody, followed by physical separation of the bound from free antigens. In some more sensitive assays (e.g., "ELISA" or "EIA") multiple steps are required. Homogeneous immunoassays, on the other hand, can distinguish between bound antigens and free ones without the need of additional separation steps. They are simple, rapid, yet more precise, more cost effective, and have the potential for total automation. For these reasons, separation-free assays are preferred in many applications such as biosensors, bioprobes and other automated instrumentation. J. P. Gosling, *Clin. Chem.*, 36:1408–1427 (1990), D. W. Chan and M. T. Perlstein, Eds., *Immunoassay. A Practical Guide* (Academic Press, New York, 1987), and E. F. Ullman and P. L. Khanna, *Methods in Enzymology*, 74:28–60 (1981).

However, because of various technical complications homogeneous systems have been difficult to obtain, with the exception of a few assays suitable only for small molecules. J. F. Burd et al., *Clin. Chem.*, 23:1402–1408 (1977), M. E. Jolley et al., *Clin. Chem.*, 27:1190–1197 (1981), and D. L. Morris et al., *Anal. Chem.*, 53:658–665 (1981).

It would be an improvement in the art to develop and characterize new fluorogenic tracer antigens that can be used as "reporter molecules" for the binding event without the need of separation steps and the labeling of antibodies. The development of such tracers could greatly facilitate the automation of a large array of clinical assays, especially of high molecular weight antigens. It would help reduce the operational time and cost, and make such assays more readily accessible to doctors and patients. Also, such tracers would be extremely useful for rapidly screening large numbers of recombinant antibodies generated with genetic engineering techniques, such as those described in C. F. Barbas et al., *Proc. Natl. Acad. Sci. USA* 89:4457–4461 (1992), R. A. Lerner et al., *Science* 258:1313–1314 (1992), and Marks et al. *J. Biol. Chem.* 267:16007–16010 (1992).

DISCLOSURE OF THE INVENTION

The invention includes a fluorogenic tracer antigen that obviates the need for separation steps or the labeling of antibodies in the performance of an assay. The tracer is a short antigen-mimicking peptide labeled with both a fluorescent energy transfer donor and fluorescent energy transfer acceptor molecules. When free in solution, the tracer exhibits very low fluorescence due to intramolecular dye dimerization. After binding to an antibody of the native antigen, fluorescence is significantly enhanced as a result of the dissociation of intramolecular dimers brought about by conformational changes in the tracer peptide.

The invention thus includes an immunoassay procedure for detecting and quantifying unknown analyte antibody or analyte antigen in bulk solution, to a reagent for use in such an immunoassay procedure, and to a process for making such a reagent. The reagent which is used in the present procedure is a peptide epitope that is recognized by the antibody in bulk solution, the peptide epitope conjugated to a pair of fluorescent energy transfer dyes capable of moving between a stacked configuration to exhibit fluorescence quenching and a spaced (unstacked) configuration to exhibit fluorescence.

A procedure for using the previously described reagent in a homogeneous antibody assay includes: placing in bulk solution a conjugate of a peptide epitope for the unknown amount of analyte antibody, and a pair of fluorescent dyes. This reagent is capable of moving between a stacked configuration to exhibit fluorescent quenching and a more spaced configuration to exhibit fluorescence. Also placed into the bulk solution is the unknown antibody which will bind with the peptide epitope which is conjugated to the pair of dyes. When this binding event occurs, the configuration of the pair of dyes will be altered between an initial stacked configuration (when in solution) to an unstacked configuration, when the epitope is bonded to the antibody, with a concomitant increase in fluorescent energy in response to the binding.

It is also within the contemplation of the invention to design a homogenous antigen assay or a homogenous DNA probe assay.

The tracers have uses including homogenous detection of macromolecules (e.g. antibodies, antigens, and DNA) of clinical interest and rapid screening of recombinant antibodies.

BEST MODE OF THE INVENTION

The "peptide epitope" used herein and to which the fluorescent dyes (preferably energy transfer dyes) are joined, either directly or through a spacer structure, is a relatively small, flexible peptide comprising alpha-amino acids which are joined together through peptide bonds. In general, there will be sufficient amino acids (e.g. from about 6 to about 13 amino acids) in the peptide to allow the peptide to fold upon itself. The term "epitope" is to be understood as relating to the specific surface of the native antigen (or "antigen") which is delineated by the area of interaction with an antibody of interest.

The peptide portion of the peptide epitope is an antigen or an antigen-mimicking peptide. Such a peptide may either be a sequential epitope which is a continuous sequence of the primary structure of the antigen; or an assembled epitope which consists of amino acids distant in the linear sequence, but brought together by tertiary structure folding. Several methods have recently emerged that enable rapid identification of high affinity binders for almost any monoclonal antibody. See, e.g. H. M. Geysen et al., *Molecular Immunology* 23:709–715 (1986), R. A. Houghten, et al., *Nature* 354, 84–86 (1991), K. S. Lam, et al., *Nature* 354:82–83 (1991) and J. K. Scott and G. P. Smith, *Science* 249:386–390 (1990).

The epitope may be chosen from any of various proteins where determining the presence of antibodies to the protein may be useful. These include epitopes from proteins associated with infectious diseases such as hepatitis B, hepatitis C, herpes simplex, and HIV. Epitopes from other useful proteins (such as rhesus factor) may also be used.

While not being bound by one theory of why the invention works so well, it is believed that antigen-mimicking peptides are more viable choices for the fluorogenic reporter molecules than their native antigens because of their small size. If a protein antigen is fluorescently-labeled, the changes in fluorescence signal (intensity, polarization, etc.) upon binding are relatively small. For this reason, previous homogeneous assays for high molecular weight antigens exhibited poor sensitivity. See, e.g. K. Nithipatikom and L. B. McGown, *Anal. Chem.*, 59:423–427 (1987). If fluorescently-labeled oligopeptides are used as tracers, however, significant changes in fluorescence signal upon binding occur presumably due to the oligopeptide's small size and chain flexibility.

The intended structure for the peptide epitope, in a preferred embodiment, can be determined by use of the epitope/mimotope screening techniques described and claimed in U.S. Pat. No. 4,833,092 to H. M. Geysen which is incorporated herein in its entirety by this reference. In such a technique, a plurality of peptides having a defined linear sequence are synthesized, contacted with the antibody of interest, and the presence or absence of binding between peptide and antibody is determined. The presence of the highest level of binding identifies the preferred candidate or candidates for the peptide epitope for use in accordance with the present invention. Once the linear sequence of amino acids in the peptide epitope has been determined, it is well within the skill of persons in the art to synthesize such a peptide epitope using solid state peptide synthesis procedures. References which discuss the various synthesis methods available include: Merrifield, *J. Am. Chem. Soc.*, 85:2149–2154 (1963); M. Bodanszky et al., *Peptide Synthesis*, John Wiley & Sons, 2d Ed., (1976), and J. Stuart et al., *Solid Phase Peptide Synthesis*, (Pierce Chemical Company, Rockford, Ill., 3d Ed.), H. Neurath et al., Eds., pp. 104–237 (Academic Press, New York, N.Y. (1976)). Appropriate protective groups for use in such synthesis procedures are also known. See the above references as well as J. F. W. McOmie, *Protective Groups in Organic Chemistry*, (Plenum Press, New York, N.Y. (1973)).

For protein antigens of unknown primary sequence or other non-protein antigens, it is still possible to screen for high affinity binders to an antibody using Geysen's method or other more recent approaches based upon peptide libraries. See, e.g. the work of R. A. Houghten, et al., *Nature*, 354: 84–86 (1991) and K. S. Lam, et al., *Nature*, 354:82–83 (1991).

Once obtained, the selected peptide epitope is then labeled with a pair of fluorescent energy transfer (namely, donor and acceptor) dyes which, when appropriately bonded to the peptide epitope to form a "conjugate", having the characteristic of dimerizing or "stacking" so as to quench any fluorescence of both fluorophores. Although, the dye pairs do not necessarily have to be fluoresence energy transfer donor and acceptors. The type of dyes which do exhibit such stacking characteristics when bonded to the peptide epitope within a sufficiently close proximity to one another include those dyes which have a generally planar aromatic structure so as to be capable of forming homo- or heterodimers when in solution at concentrations which are sufficiently high (for example, $10^{-3}$ to $10^{-4}$ M).

It is well known that some fluorescent dyes (fluoresceins, rhodamines, cyanines, etc.) form dimers in aqueous solution when they are within close proximity of each other.

K. K. Rohatgi and G. S. Singhal, *J. Phys. Chem.*, 70:1695–1701 (1966), K. K. Rohatgi and A. K. Mukhopadhyay, *Chemical Physics Letters*, 12:259–260 (1971), and W. West and S. Pearce, *J. Phys. Chem.*, 69:1894–1903 (1965). Due to the interaction between transition dipoles of the resonating dimeric structure, these dimers exhibit very low fluorescence quantum yields. I. L. Arbeloa, *J. Chem. Soc. Faraday Trans.*, 2:1735–1742 (1981), I. L. Arbeloa, *J. Chem. Soc. Faraday Trans.*, 2 77:1725–1733 (1981), and I. L. Arbeloa and P. R. Ojeda, *Chemical Physics Letters*, 87:556–560 (1982). The monomers of these dyes, however, are highly fluorescent in aqueous solutions. For this reason, dye dimerization has largely been regarded as an adverse effect in biological applications. Bailey et al., *J. Pharm. & Biomed. Anal.*, 5:649–658 (1987). This invention uses this phenomenon to advantage. If two fluorescent dyes are conjugated to both ends of an antigen-mimicking peptide, it is probable that intramolecular dimers will form because of the planar structure of dyes and the short effective distance. This will result in significant fluorescence quenching. Upon binding to its antibody, however, the dye-peptide conjugate is expected to undergo conformational changes to accommodate to the active site. The fluorescence intensity will be enhanced as a result of dissociation of the intramolecular dimers.

Fluorescent energy transfer dyes of the fluorescein family, such as fluorescein, TMR, rhodamine B, and Texas Red are representative dyes of this type. Due to the interactions between the transition dipoles of the resonating dimeric structure, the fluorescent quantum yield of the dimer will be quite low when no antibody which can bind to the peptide epitope is present as compared to the significantly higher fluorescence quantum yield in aqueous solution when undimerized after the peptide epitope has become bound to the antibody. In this manner, a homogeneous antibody assay can be designed wherein labeled peptide epitope is placed in solution and the antibody analyte is added so that the antibody and peptide bind, causing the dimerization to decrease with an attendant increase in fluorescence.

Fluorescein and TMR were used herein as the labels since, among other things, they are a well-characterized fluorescence energy transfer pair as well. Because this property may increase the Stoke's shift of the fluorescence emission, it is useful in reducing interference from scattering or serum fluorescence.

The invention is not limited to using fluorescent dyes. Organic ligands of some lanthanide metals, such as europium (Eu3+) and terbium (Tb3+) may also be used as labels. E. P. Diamandis, *Clin. Chem.*, 37:1486–1491 (1991). In the absence of antibodies, the peptide forms an intramolecular coordination complex with these ions. Such a complex is highly fluorescent and has fluorescence lifetimes ranging from $\mu$s to ms. If the peptide changes its conformation from a folded to a more extended state upon binding to its antibody, the coordination bonds with the metal could be broken, thus making the peptide non-fluorescent. Therefore, the fraction of bound and free tracers can be related to the net change in fluorescence intensities. Molecular dynamics and Monte Carlo simulations of the free peptide have shown that the distance between —SH and —NH2 groups is about 10 Å for the energy minimized conformational states. If coordination ligands, e.g., acetyl acetone or dipyridylamine, are introduced at these positions, they should fall within the coordination distance with Eu3+ or Tb3+. The extended length of a 13-mer peptide is about 50 Å which is far enough to break the coordination bond to release the ion, resulting in a dark species.

Solutions for use with the invention are ones in which the labeled peptide epitope and antibodies can be incorporated. They are generally buffered aqueous solutions and include buffered normal saline with a pH of 6 to 8.

A homogeneous antigen assay can also be designed wherein the aqueous solution contains antibodies and doubly labeled peptide epitope bound together so that the amount of intramolecular dimer formation is low thereby producing a high fluorescence signal. The addition of unlabeled analyte ligand, which binds to the antibody bonded to the peptide epitope, will result in a certain fraction of the doubly labeled peptide epitope being displaced from the antibody bringing about a concomitant decrease in fluorescence resulting from the formation of dimers in the labeled peptide epitope as it is displaced from the antibody.

Homogeneous assays can, therefore, be achieved by toggling the intramolecular monomer <==> dimer equilibrium through t he antibody-antigen binding event. For antibody assays, the sample is added to a solution of doubly-labeled peptide, and the net fluorescence increase is related to the antibody concentration.

For antigen assays, the sample is add ed to a solution of antibody mixed with the doubly-labeled tracer, and the net fluorescence decrease is related to the analyte concentration.

In analogy to the antibody-antigen system, this principle may also be utilized in DNA assays. If a DNA probe is used t o link the two fluorophores, hybridizing with its target DNA will bring about a transition from intramolecular dimers to monomers. The target DNA can therefore be measured from the net increase in fluorescence intensity.

It is broadly within the scope of the present invention to immobilize the peptide epitope containing the pair of fluorescent energy transfer dyes which are capable of moving between stacked and unstacked configurations, on a waveguide through which light can be shown to generate an evanescent wave in the bulk solution. It is within this are a of the evanescent wave that the fluorescent energy transfer characteristics of the selected dyes can be monitored to appropriately detect antigen-antibody binding events and thereby perform the immunoassay. However, a heterogeneous assay format is not the preferred embodiment. A homogeneous assay is preferred in view of simplicity and the absence of potential background signals due to the presence of the support as is well known to persons of ordinary skill in the art.

The fluorogenic tracer antigen described has many potential applications. First, its simplicity, speed, and sensitivity allow adaptation to existing automated instrumentation, such as the 96-well fluorescence plate reader or the TDX fluorescence polarization analyzer. Second, because labels all reside on the tracer peptide, fluorescent labeling of antibodies becomes unnecessary, thus eliminating the problem of reduced antibody activity often encountered. See, e.g. E. F. Ullman and P. L. Khanna, supra. Third, the doubly-labeled peptide has very long Stoke's shift. If an argon ion laser (488 nm line) is used as the excitation source, the fluorescence emission can be measured at 576 nm, instead of 515 nm. The Stoke's shift of ca. 90 nm helps to avoid interference from scattering and visible serum fluorescence at 500–515 nm. Fourth, since the fluorescein fluorescence (515 nm) remains constant after binding, it may be used as an internal self-reference point to correct for instrument fluctuations. Making use of this feature may also eliminate the need for standard curves in automated instruments. Fifth, in evanescent immunosensors, interference from bulk fluorescence is often a serious problem. See, e.g. V. Hlady et al., in *Surface and Interfacial Aspects of Biomedical Polymers: Protein Adsorption*, J. D. Andrade, Ed. (Plenum Press, New York, 1985), pp. 81–119. If the doubly-labeled peptide is used as a tracer, it is fluorescent only when bound to immobilized antibodies and would become non-fluorescent when displaced into bulk solution, thus there should be no problem of bulk fluorescence. This would significantly reduce the stringency required for the optic detection system. Sixth, different fluorescent dye pairs may be labeled onto different tracer peptides, thus proving the possibility of detecting several analytes in the same sample simultaneously. Seventh, this concept may also be applied to the homogeneous detection of polynucleotides hybridization using a DNA probe labeled with two fluorophores.

The present invention is further illustrated with the following Examples:

EXAMPLE I

The hCG Epitope Peptide and its Conjugate with Dyes

Figure 1:
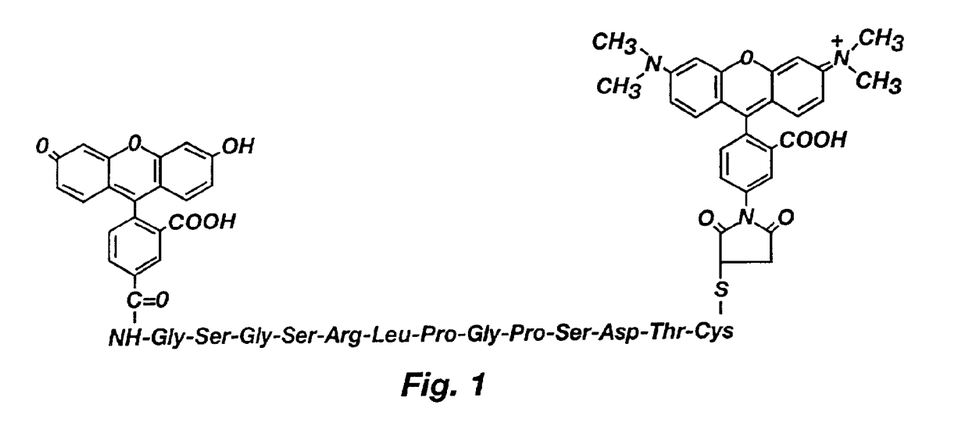
FIG. 1 depicts a doubly labeled oligopeptide useful in the practice of one embodiment of the invention.

A peptide from human chorionic gonadotrophin (hCG) was used as the spacer between fluorescein (F) and tetramethylrhodamine (T). Depicted in FIG. 1 is the structure of a hCG epitope peptide labeled with fluorescein and TMR. The peptide was identified by screening 221 (24) overlapping octapeptides synthesized on the tips of 96-pin solid supports as described in H. M. Geysen et al., *Molecular Immunology*, 23:709–715 (1986).

According to the Geysen method, a series of n-8 overlapping octapeptides were synthesized on the tips of 96-pin solid supports and tested for specific binding with anti-hCG using a ELISA procedure, where n is the number of amino acid residues in a sequence. A total number of 221 octapeptides was screened because hCG has two chains and a total number of 237 amino acid residues: R. B. Carlsen et al., *J. Biol. Chem.*, 248:6810–6827 (1973); R. Bellisario et al., *J. Biol. Chem.*, 248:6796–6809 (1973).

A core sequence of RLPGPSD (SEQ ID NO:1) showed strong reaction with the anti-hCG Mab. In order to conjugate dyes to the peptide without compromising its binding properties, the sequence GSGSRLPGPSDTC was synthesized using standard Fmoc methodology (J. M. Stewart and J. D. Young, Eds., *Solid Phase Peptide Synthesis* (Pierce, Rockford, Ill., 1984)) and purified on reversed phase HPLC to >95% purity. Its chemical identity was confirmed by Fab mass spectra and amino acid analysis. The peptide was first reacted with TMR maleimide in 50 mM, pH 6 phosphate buffer for 48 hours to make oligopeptide labeled with TMR ("pepT"). All chemically reactive dyes used were purchased from Molecular Probes, Eugene, OR. After purification on reversed phase FPLC (C-18 column, particle size 15 mm, Pharmacia LKB), pepT was reacted with fluorescein succimidyl esters in 50 mM borate buffer, pH 8.5 for overnight to make FpepT. The dye-peptide conjugate has the chemical structure of F-GSGSRLPGPSDTC-T (SEQ ID NO:2) (FpepT) and is shown in FIG. 1. A gradient of acetonitrile in water was used to purify these conjugates. In a typical elution, the acetonitrile content was increased from 15% to 30% over a period of 20 minutes, followed by an isocratic elution at 30% acetonitrile. All solvents contained 0.1% trifluoroacetic acid. The molecular weight of FpepT measured by Fab mass spectra was 2091 which is 18 mass unit higher than the expected value of 2073.19. The hydrophilicity of the peptide plus the bulky fluorophores probably has caused entrapment of a bonded water molecule inside the conjugate.

Except for Cys, the linker peptide sequence corresponds to a portion of the naturally occurring sequence near the C-terminus of hCG b chain. This sequence, rather than the core peptide, was used because the latter exhibited little affinity to the anti-hCG Mab after fluorescein is attached at its N-terminus.

Comparison of the absorption spectra of FpepT, Fpep, and pepT showed that the major absorption peak of fluorescein blue-shifted by 2 nm, while that of rhodamine red-shifted by 9 nm. Also, the long wavelength peak of rhodamine had actually become hypochromic by a factor of 1.6.

There are normally two electronic transitions in the visible absorption region of fluoresceins and rhodamines: upper and lower energy levels. The absorption spectrum of a monomer consists of an intense band at the longer wavelength and a shoulder at the short wavelength. The formation of dimers provides a "flip-flop" of these relative peak intensities so that the shorter wavelength transition is more hyperchromic. The changes in these two excited levels of the dimer have significant consequences on its fluorescence spectra. The hypochromativity of the longer wavelength transition suggests a relatively long lifetime of the lower energy level. Due to radiation-less transitions from the upper to the lower excited level, most of the dimer molecules are in the lower state which exhibits weak fluorescence emission. Therefore, this radiation-less relaxation process substantially contributes to the low fluorescence quantum yield of the dimer.

Because of these changes, the absorption spectra of FpepT exhibited a poor fit to the simple sum of those of Fpep and pepT (FIG. 2), suggesting that ground-state static interactions exist between F and T. These static interactions have significant effect on the fluorescence quenching.

Figure 2:
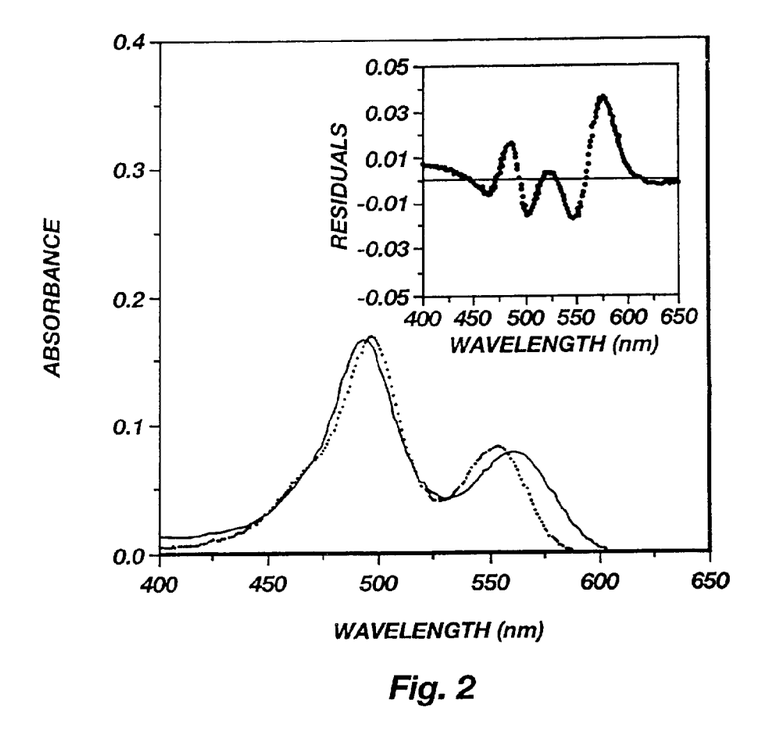
FIG. 2 is a graph depicting the absorption spectra of the FpepT conjugate (solid line).

FIG. 2 graphically depicts the absorption spectra of the FpepT conjugate (solid line). The dashed line shows a least-square fit of the spectra with a model assuming a simple mixture of Fpep and pepT according to the method of Wei, et al. *Biosensor Design and Application*, P. R. Mathewson and J. W. Finley, Eds. (American Chemical Society, Washington, D.C., 1992), vol. 511, pp. 105–120. The residual between the measured value and the fitted value at each wavelength is given in the inset. Because a perfect fit would generate a random residual plot with the average being zero, the systematic residual pattern in this figure indicates significant ground-state interactions between the two dyes in the same molecule. The concentration of this conjugate was determined by its absorbance at 560 nm using the molar extinction coefficient of 60,000 M−1 cm−1. The buffer system used for this spectra and all other subsequent fluorescent studies was 100 mM phosphate buffer, pH 7.4, unless otherwise stated.

Figure 3:
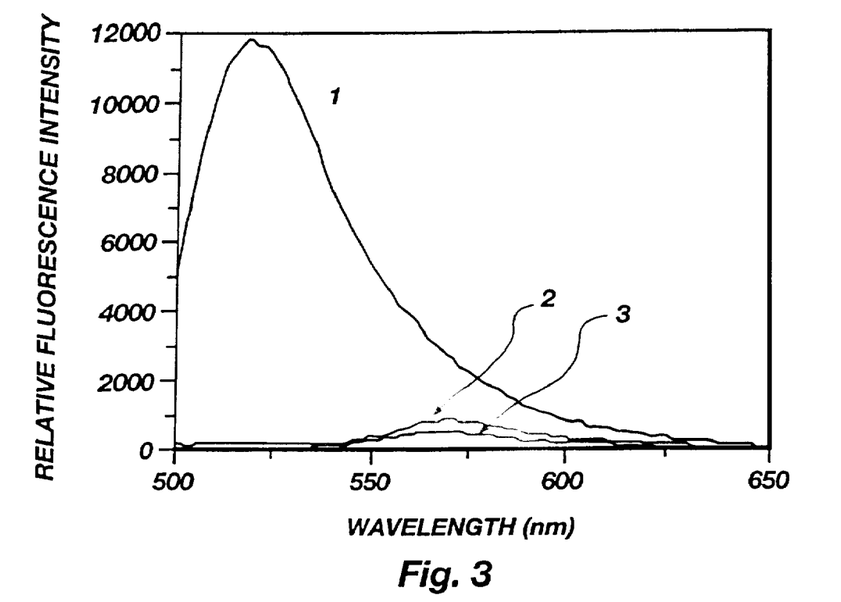
FIG. 3 is a graph depicting the relative fluoresence intensity vs. wavelength.

FIG. 3 depicts the technical fluorescence spectra of Fpep (1), pepT (2) and FpepT (3) when excited at 493 nm (c.a. 10–7 M). Compared to Fpep, the fluorescein fluorescence is quenched by 98% in FpepT.

Figure 4:
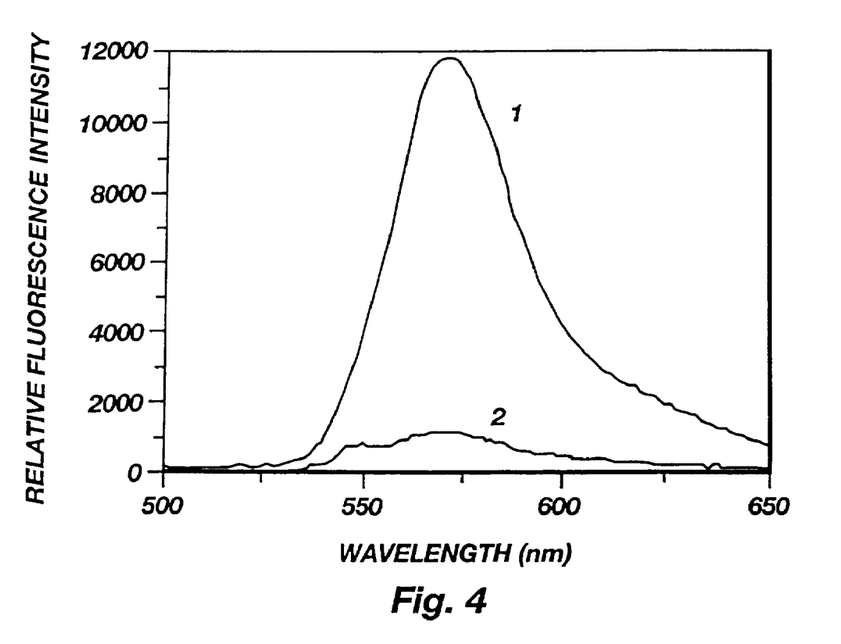
FIG. 4 is a graph depicting the relative fluoresence intensity vs. wavelength.

FIG. 4 depicts the technical fluorescence spectra of pepT (1) and FpepT (2) when excited at 550 nm (c.a. 10–7 M). Compared to pepT, the rhodamine fluorescence is quenched by 90% in FpepT. All fluorescence measurements (spectra, intensity, and polarization) were made with an ISS PC-1 fluorometer (ISS, Champaign, Ill.) at 6° C. unless otherwise indicated.

FIG. 3 shows that the intrinsic fluorescence of rhodamine in the FpepT conjugate is 10 fold lower than in the absence of F (i.e., 90% quenching) as a result of contacting with fluorescein. The fluorescein fluorescence of FpepT, on the other hand, is 64 fold lower than in the absence of T (i.e., 98% quenching). The higher quenching efficiency of the fluorescein fluorescence results from both the static interaction with and excited-stated energy transfer to rhodamine. These results strongly suggest that free FpepT indeed exists as intramolecular dimers.

EXAMPLE II

Binding of FpepT with Anti-hCG Mab

Figure 5:
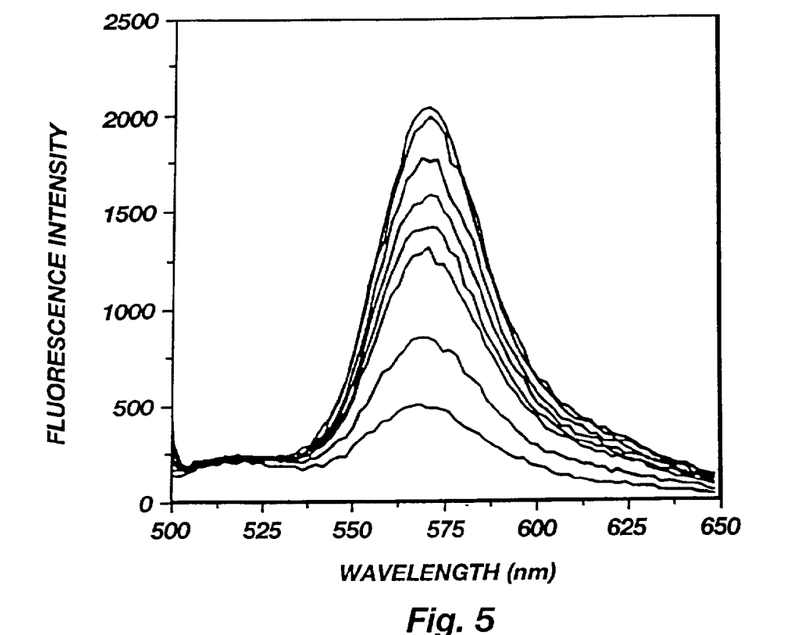
FIG. 5 graphically depicts the technical fluorescence spectra of FpepT ($10^{-7}$ M) as 5 $\mu l$ aliquots of stock anti-hCG Mab were added. The total anti-hCG concentration changed from zero to $2.6 \times 10^{-7}$ M at an increment of $3.7 \times 10^{-8}$ M with a dilution factor of 2%.

The fluorescence spectra of FpepT upon binding to the anti-hCG Nab is presented in FIG. 5. The fluorescence of rhodamine (lambda max=570 nm) increased up to 5 fold with increasing antibody concentration as a result of diminished interactions with fluorescein. The fluorescein fluorescence (lambda max=515 nm), on the other hand, remained constant and quenched because of the fluorescence energy transfer from F to T. Since the distance at which 50% energy transfer efficiency occurs is 54 Å for the F-T pair, even if the peptide became fully extended after binding, the end-to-end distance of 47.19 Å would still allow 70% energy transfer efficiency. For this reason, the fluorescein fluorescence was not enhanced although the static quenching should be equally reduced for fluorescein as for rhodamine. The reduced ground state interaction between the two dyes can also be seen by comparing the absorption spectra of FpepT in the presence and absence of antibody.

Figure 6:
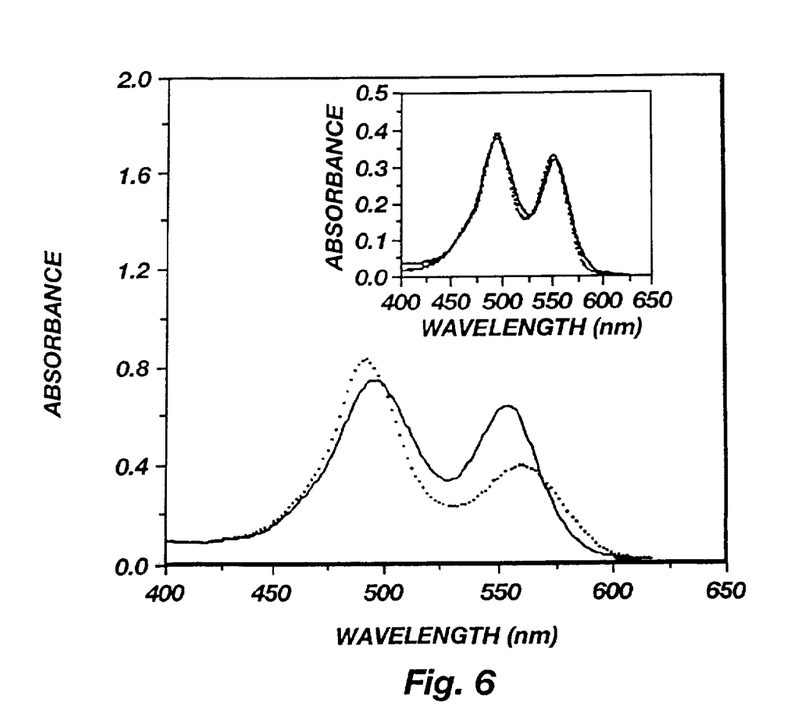
FIG. 6 is a comparison of the absorption spectra of FpepT ($6.5 \times 10^{-6}$ M) in the absence (dashed) and presence (solid) of anti-hCG antibodies ($7.5 \times 10^{-6}$ M).

FIG. 6 compares the absorption spectra of FpepT (6.5×10−6 M) in the absence (dashed) and presence (solid) of anti-hCG antibodies (7.5×10−6 M). After binding, the major absorption peaks of fluorescein and rhodamine have shifted more towards each other. As a result, the spectra can be better fitted with a model assuming a simple mixture of Fpep and pepT as shown in the inset. A.-P. Wei et al., in *Biosensor Design and Application*, P. R. Mathewson and J. W. Finley, Eds. (American Chemical Society, Washington, D.C., 1992), vol. 511, pp. 105–120. An anti-hCG monoclonal antibody from Organon Teknika, Boxtel, the Netherlands was used. It had been prepared according to the procedure of R. v. Erp et al., *J. Immunol. Methods*, 140:235–241 (1991). Antibody concentration was determined from its absorption at 278 nm, using an extinction coefficient of 14. Mouse immunoglobulin and bovine serum albumin were purchased from Sigma Chemical Co. (St. Louis, Mo.).

As shown in FIG. 6, the major absorption peaks of fluorescein and rhodamine have shifted toward each other after binding. And, the absorptivity of the rhodamine moiety has increased by a factor of 1.6 because of dimer dissociation. As a result, the spectra could be better approximated by a simple mixture of the two respective dyes (FIG. 6, inset), indicating that the bound form of FpepT has less spectral perturbation than the free species. It should be noted, however, that the measured spectra of the bound species do not completely coincide with the fitted spectra due to residual spectral perturbations that still exist.

Figure 7:
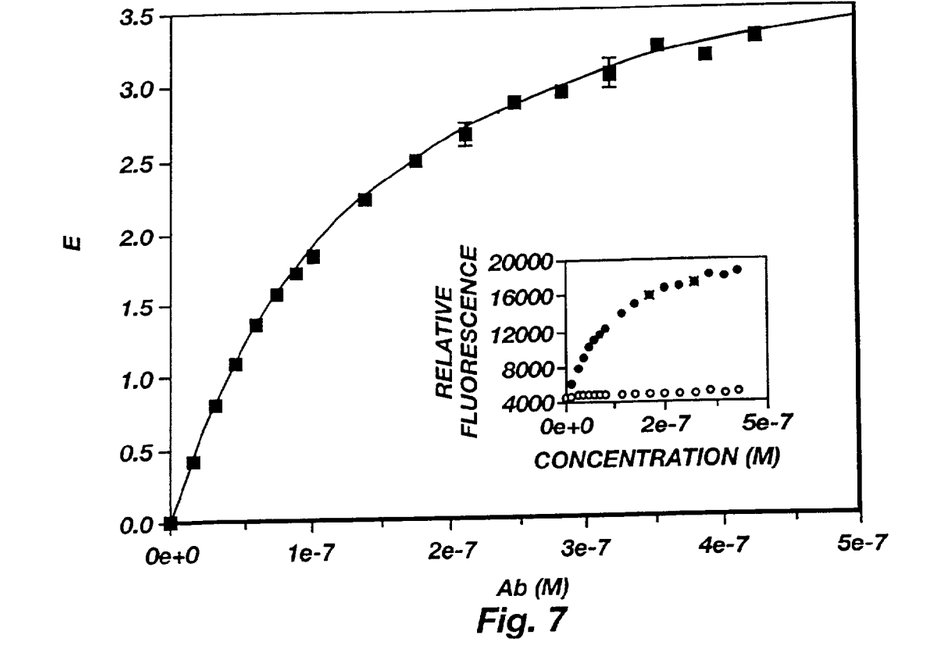
FIG. 7 depicts graphically the fluorescence enhancement factor E as a function of antibody concentration (EX=493 nm and EM=590 nm).u FIG. 8 graphically depicts the fluorescence intensities as a function of FpepT concentration (EX=561 nm and EM=590 nm).

A typical intensity-versus-antibody concentration profile for the binding of FpepT with anti-hCG Mab is presented in FIG. 7. FIG. 7 depicts graphically the fluorescence enhancement factor E as a function of antibody concentration (EX=493 nm and EM=590 nm). Fluorescence intensities of FpepT (1.3×10−7 M) in sample (Is, filled circle) and reference (Ir, open circle) cuvettes as aliquots of stock anti-hCG and BSA & mouse IgG solutions were added are shown in the inset. The value of E was calculated from:

$$E = \frac{Is - Ir}{Ir}$$

The E~Po curve was fitted with the following equation using Kaleidagraph (Abelbeck Software):

$$2Po = \frac{KdE}{Em - E} + \frac{LoE}{Em}$$

where Po, Lo, Em and Kd are the total antibody concentration, total FpepT concentration, maximum enhancement, and dissociation constant, respectively. The values of Kd and Em were found to be Kd=2.2×10−7 M and Em=4.1, respectively. A higher value of Em (Em=6.8) was obtained for EX=561 nm and EM=590 nm.

While the addition of anti-hCG resulted in gradual increase in fluorescence, the same amount of bovine serum albumin and nonspecific mouse IgG did not have any effect on the fluorescence of FpepT, indicating that the enhanced fluorescence is a result of specific binding. The fluorescence enhancement factor (E) as a function of antibody concentration (Po) was fitted with a classical binding equation (FIG. 7, inset). The maximum enhancement (Em) at 590 nm was found to be 6.8 (ex=561), 4.1 (ex=493, data not shown), respectively. The dissociation constant (Kd) was (2.2±0.3)×10−7 M (N=6). When the same peptide was studied in the absence of fluorescein (i.e. with only rhodamine at the Cys position), the value of Kd was found to be 0.67×10−7 M.

The three-fold decrease in binding affinity after labeling with fluorescein was probably caused by either steric hindrance or conformational differences between these two labeled forms of the peptide.

Compared to FIGS. 3 & 4, Em values of 4.1 and 6.8 should correspond to 51% and 78% of the intrinsic fluorescence of TMR, respectively. Results of control experiments confirmed this prediction. In a separate binding experiment, an antibody solution of fixed concentration was titrated with aliquots of FpepT. The curve of E vs. FpepT concentration (Lo) was fitted with a classical binding equation (FIG. 8).

Figure 8:
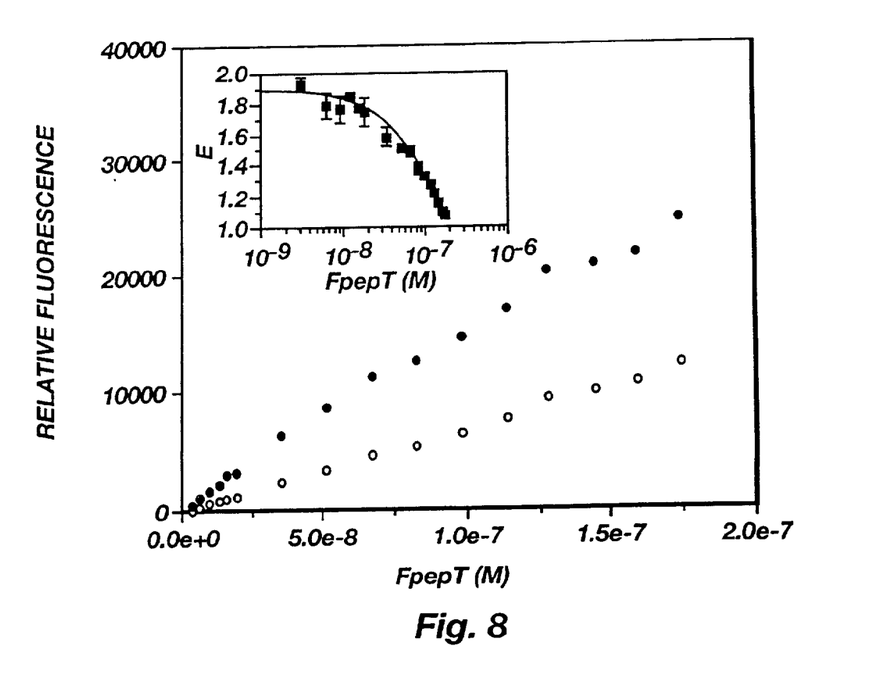

FIG. 8. graphically depicts the fluorescence intensities as a function of FpepT concentration (EX=561 nm and EM=590 nm). Sample cuvette contained 1.4×10−7 M anti-hCG, and the reference cuvette contained 1.5×10−5 M of BSA and mouse IgG. The Lo~E curve was fitted with the binding equation using Kaleidagraph (inset):

$$Lo = 2Po\frac{Em}{E} - \frac{KdEm}{Em - E}$$

The value of Kd was (2.1±0.4)×10−7 M (N=3), in excellent agreement with the result of FIG. 7.

EXAMPLE III

Binding Specificity and Reversibility

Aliquots of hCG were added to a mixture of FpepT and anti-hCG to displace FpepT from the antibody. As the hCG concentration was increased, a series of spectra similar to FIG. 5 but in reverse order were obtained, indicating the bound fraction of FpepT was decreased (spectra not shown).

Figure 9:
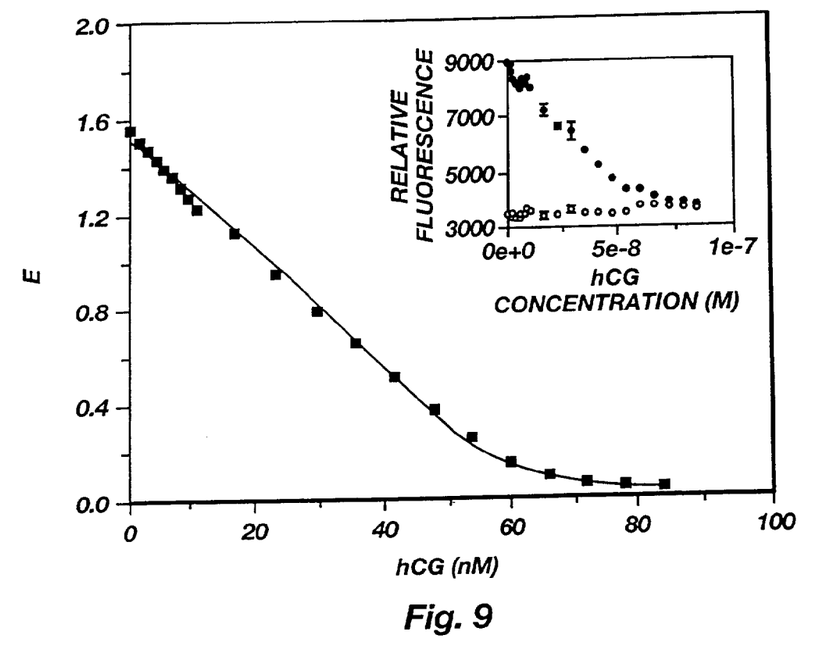
FIG. 9 graphically depicts the exchange of FpepT by hCG (EX=561 nm and EM=590 nm) in an antigen assay according to the invention.

FIG. 9. graphically depicts the exchange of FpepT by hCG (EX=561 nm and EM=590 nm). A mixture of FpepT (5.5×10−8 M) and anti-hCG Mab (4.5×10−8 M) was first prepared, and 5 µl aliquots of hCG stock solution (1100 IU/ml) were added to the mixture. The reference cuvett contained only FpepT without antibody. The decrease in fluorescence intensity (inset) is due to displacement of FpepT by hCG. The fraction of bound FpepT (f2=E/Em) and the total hCG concentration (L°1) follows the equation:

$$L°1 = \left[\frac{K1(Em - E)}{K2E} + 1\right]\left[2Po - \frac{K2E}{Em - E} - (L°2)\frac{E}{Em}\right]$$

where K1, K2, Po, and (L°2) are the disassociation constants of hCG and FpepT, total antibody concentration, and total FpepT concentration, respectively. The data set of E vs. hCG(l°1) was fitted with the above model. The values of K1, K2 were found to be 4.9×10−10 M and 2.4×10−7 M, respectively. Human chorionic gonadotrophin (hCG) was a gift from Organon Teknika, Boxtel, the Netherlands. The concentration of hCG was converted from IU/ml to mole/l using a specific activity of 11,200 IU/mg for highly purified hCG and a molecular weight of 38,000.

FIG. 9 shows the fluorescence intensity as a function of concentrations of hCG, BSA & mouse IgG. The decrease in fluorescence at 590 nm is only specific to hCG, and little change was brought about by the non-specific proteins. These results confirmed the expectation that FpepT binds specifically to the same active site as hCG. The enhancement factor (E) vs. hCG concentration was fitted with a binding equation. The values of Kd for hCG and FpepT were found to be 4.9×10−10 M and 2.4×10−7 M, respectively. In spite of the 490-fold lower affinity exhibited by the tracer, the lowest detection limit of hCG was about 1×10−9 M. This excellent assay performance is attributed to the fluorogenic properties which allow preferential measurements of the bound tracer.

EXAMPLE IV

Fluorescence Anisotropy

Figure 10:
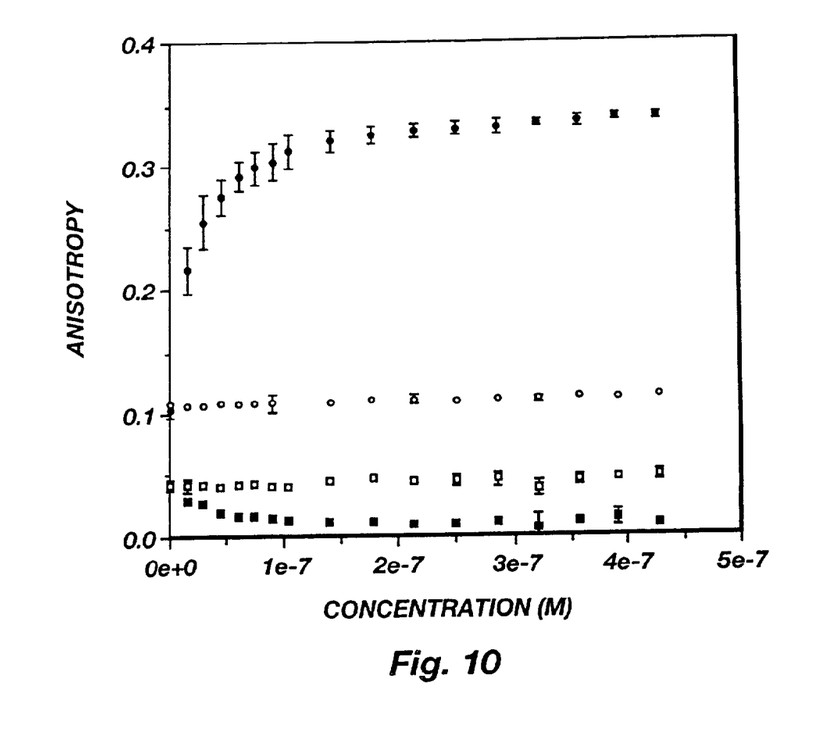
FIG. 10 is a graph depicting the fluorescence anisotropy of FpepT ($1.6 \times 10^{-8}$ M).

The anisotropy of rhodamine when excited at 550 nm as a function of anti-hCG concentration is shown in FIG. 10. In FIG. 7, (for excitation at 550 nm) anisotropies at 590 nm as a function of concentrations of anti-hCG and BSA & IgG are shown as filled and open circles, respectively. The error bars represent the standard deviations of three different experiments. The free FpepT has an anisotropy value of Af=0.1087±0.0014 (N=17). The anisotropy value for bound FpepT is Ab=0.3444. Similar results were obtained for ex=490 nm and em=515 nm (not shown). For excitation at 490 nm, anisotropies at 590 nm as a function of concentrations of anti-hCG and BSA & IgG are shown as filled and open squares, respectively. This property can be used for a fluoresence polarization assay.

The more than 3-fold increase in anisotropy was attributed to the large difference in size between FpepT (MW=ca. 2000) and the antibody (MW=ca. 150,000). Similar result was obtained for the anisotropy of fluorescein when excited at 490 nm (data not shown). Because the emission was from the low-energy absorption band in these measurements, the limiting anisotropy value is expected to be in the range of 0.39–0.4 for both fluorophores. If the rotational diffusion of the intact IgG and the Fab fragments is taken into account, the observed maximum anisotropy value of 0.3444 for the bound FpepT suggests that both fluorophores have little rotational mobility in the antibody-FpepT complex, because of the small sized antibody active site and the bulky fluorophores.

If, however, the excitation was 490 nm and fluorescence was measured at the rhodamine emission, a completely different trend of change in anisotropy was obtained. Under this condition, because the high-energy absorption band was excited, the anisotropy is more a measure of the angle between the absorption and emission dipoles. The anisotropy of the free FpepT was 0.0436 . 0.0023 (N=17), as compared to 0.1087±0.0014 (N=17) when excited at 550 nm. The depolarization effect is caused by the non-colinearity between the absorption dipole at 490 nm and the emission dipole. As the anti-hCG concentration was increased, if there were no change in the angle between these two dipoles, an increase in anisotropy due to the diminished rotational motion would be expected. However, the data shows that increasing amount of antibody actually results in a gradual decrease in the anisotropy which saturates at near zero. This phenomenon strongly indicates that the angle between the two dipoles of FpepT had actually become larger when bound.

These results, together with those depicted in FIGS. 5 and 6, point to the fact that the observed fluorescence enhancement was indeed due to the dissociation of the intramolecular dimers between fluorescein and rhodamine as a result of conformational changes in FpepT.

EXAMPLE V

Fluorescein/anti-fluorescein as a Model System

Figure 11:
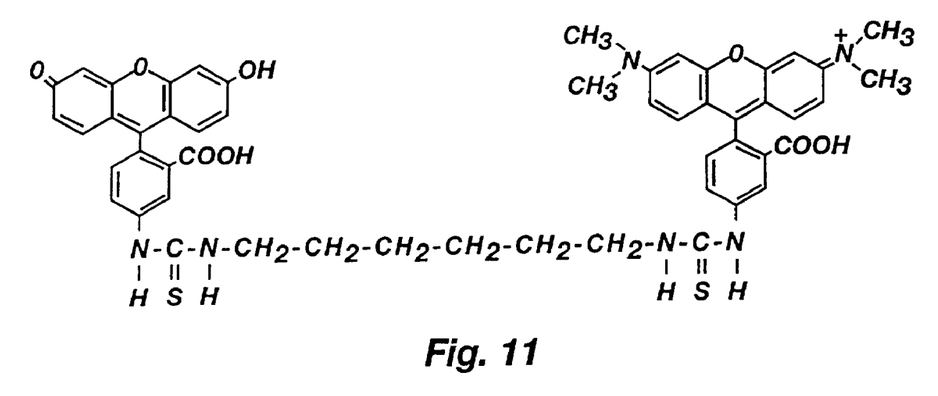
FIG. 11 depicts the chemical structure of a dimeric conjugate consisting of fluorescein and tetramethylrhodamine ("TMR") linked via a hexane spacer in a model system.
Figure 12:
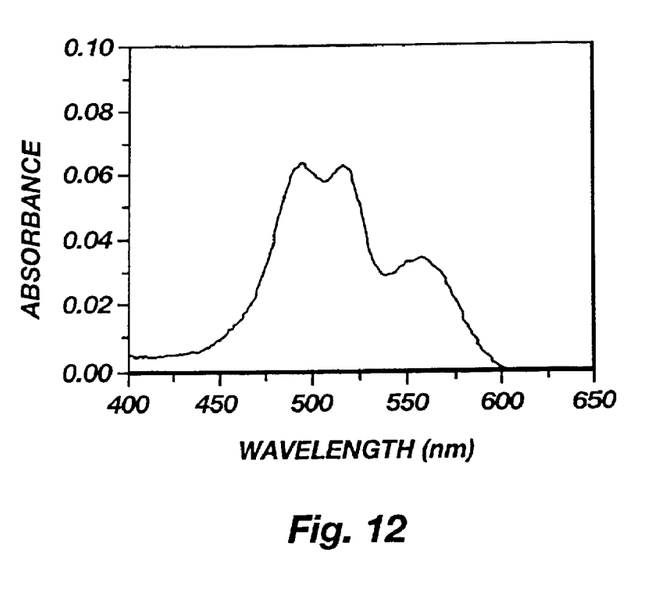
FIG. 12 is the absorption spectra of the conjugate shown in FIG. 11.

In addition to the hCG/anti-hCG system, a model system was also studied which consists of an anti-fluorescein Mab (4-4-20) and an antigen made of fluorescein linked to rhodamine via a hexane spacer (i.e. FhexT). The structure of this conjugate is shown in FIG. 11. To make FhexT, diaminohexane was reacted with an equal molar mixture of 5-isothiocynates of fluorescein and TMR in 100 mM carbonate buffer, pH 9.5 for overnight. The FhexT conjugate was isolated from the reaction mixture on reversed phase FPLC using the same condition as in FIG. 2. The absorption spectra of this conjugate is shown in FIG. 12. The bands at 515 nm and 555 nm are characteristic of the spectral splitting due to ring stacking as observed for rhodamine homo-dimers. I. L. Arbeloa and P. R. Ojeda, *Chemical Physics Letters* 87:556–560 (1982).

Figure 13:
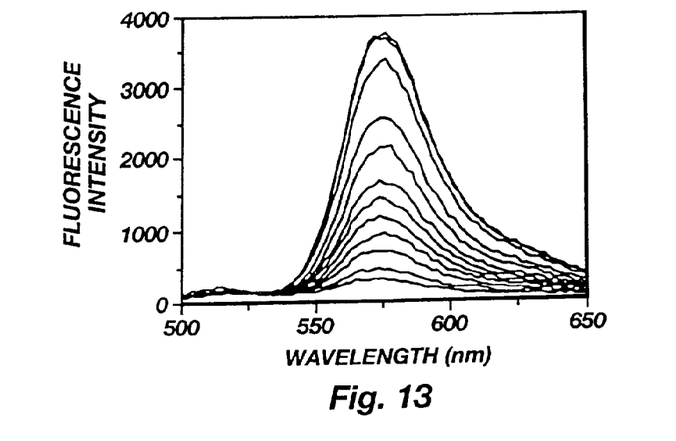
FIG. 13 depicts the technical fluorescence spectra of the FhexT conjugate (4.35×10–7 M) as aliquots of (Fab')2 fragment of antifluorescein 4-4-20 were added.
Figure 14:
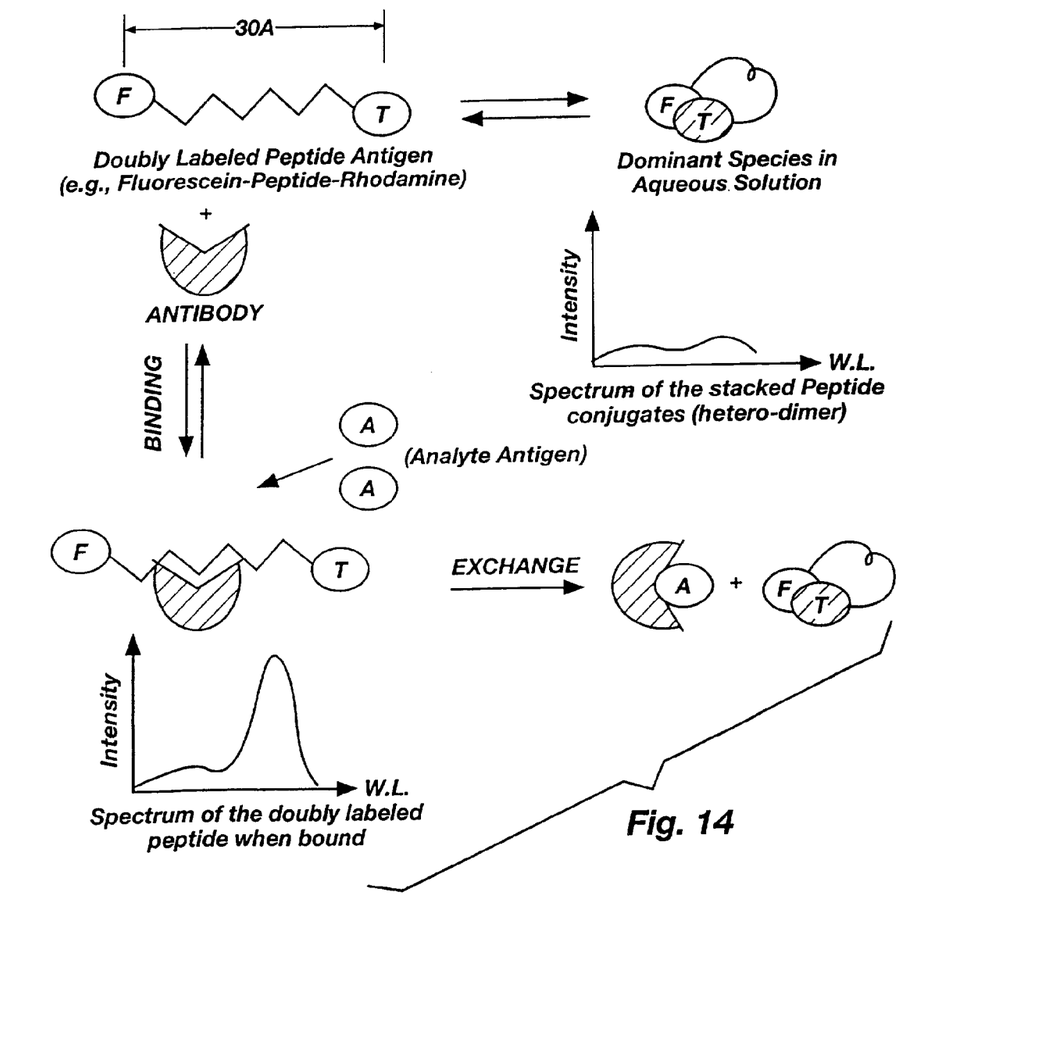
FIG. 14 schematically represents the invention.

Concentrations of the conjugates used in FIG. 12 were determined from the absorbance at 556 nm using the extinction coefficient of 58,000 M−1 cm−1. In this particular case, however, the ring stacking is due to the formation of fluorescein-rhodamine hetero-dimers. Another indication of stacked dimer formation was the low level of fluorescence observed for FhexT. The fluorescence of free fluorescein or rhodamine at the same concentration would be about 1000-fold higher than that of the conjugate. As shown in FIG. 13, the fluorescence of rhodamine (lambda max=576 nm) increased with increasing concentrations of (Fab')2, an antigen-binding fragment of 4-4-20, while that of fluorescein (lambda max=515 nm) remains at a constant low level. This observation is consistent with the results of FIGS. 5 and 6, except that the enhancement in this case is about 400-fold, rather than 5-fold. This difference is attributed to two factors. First, the close distance between the two dyes in FhexT (~10 Å) allows almost 100% energy transfer efficiency from fluorescein to rhodamine. It also facilitates stacked dimer formation which quenches fluorescence more efficiently. Second, because fluorescein is the antigen in this system, it fits tightly into the binding site of the 4-4-20 Mab. J. N. Herron et al., *Proteins: Structure, Function, and Genetics*, 5:271–280 (1989). The static interaction with rhodamine after binding is thus diminished more effectively in this system than in the hCG/anti-hCG system. For these reasons, much higher enhancement of rhodamine fluorescence was observed. Binding specificity and reversibility of FhexT with 4-4-20 (Fab')2 was studied using 5-aminofluorescein æ a nonfluorescent derivative of fluorescein. J. N. Herron, in *Fluorescein Hapten: An Immunological Probe*, J. E. W. Voss, Eds. (CRC Press, 1981) pp. 53–55.

The FhexT-antibody complex from the above titration experiments (FIG. 12) were titrated with 10 ml aliquots of 5-aminofluorescein (10-4M) in order to exchange the FhexT. Measurements were made after stirring for 2 minutes in the cuvette holder at 25° C. Spectra measured after 2 minutes and 30 minutes were found to be completely superimposable, indicating that binding equilibrium was achieved in a period of less than 2 min.

FIG. 13 is the technical fluorescence spectra of the FhexT conjugate (4.35×10−7 M) as aliquots of (Fab')2 fragment of antifluorescein 4-4-20 were added. The total (Fab')2 concentration changed from zero to 2.6×10−7 M with a dilution factor of 3.6%. The concentration of (Fab')2 was determined by absorbance at 278 nm using an extinction coefficient of 1.5 and molecular weight of 110,000 daltons.

A series of spectra similar to FIG. 13 but in reverse order were obtained as increasing amount of aminofluorescein was added, resulting a typical exchange curve (data not shown). BSA was found to have no effect on the fluorescence intensity of FhexT in either bound or unbound state. These results indicate that the FhexT tracer binds to 4-4-20 specifically and reversibly. Although the FhexT/4-4-20 system needs to be further characterized to obtain biophysical parameters, it certainly serves as a template for optimizing the FpepT tracer or developing other tracers because of the efficient quenching and dramatic enhancement of fluorescence it exhibited.

Generality and Fluorophore Selection

The hCG/anti-hCG system described herein was completely a random choice. From this stand-point, these results should be of general applicability. Although the hCG epitope was identified based upon the hCG sequence, recent peptide technologies have made it possible to identify a high affinity antigen-mimicking peptide for any monoclonal antibody. It therefore follows that the inventive approach may also be applied to protein antigens of unknown sequence or other non-protein antigens. Proper labeling of the peptide with fluorophores is the most critical aspect of these fluorogenic tracers. Although the core peptide is usually 6 to 8 amino residues in length, a longer sequence is needed in order to reduce steric hindrance. The length of peptide will, in turn, determine what fluorophores to use. Assuming a typical dimerization constant of 2,500 M−1, the concentration of fluorescent dyes required to form 90% dimers is $1.8 \times 10^{-2}$ M which is $1 \times 10^{19}$ molecules/cm3. Under this condition, the average distance between two dye molecules is about 60 Å (measured from the centers of mass). Since the extended distance between alpha-carbons in polypeptide is 3.63 Å, the distance of 60 Å corresponds to about 16 amino acid residues. In other words, if the dye has a Kd of 2,500 M−1, the two fluorophores in the tracer can be spaced, at most, by 16 residues. This provides the basis for selecting fluorophores for a given peptide length. If the peptide is shorter than a 16-mer, fluorophores with smaller Kd should be used, and the vice versa, in order to achieve effective intramolecular dimerization. The dimerization constants of fluorescein, eosin, rhodamine B, rhodamine 6G are 5, 110, 2100, 5600 M−1, respectively (22, 33, 34), while that of cyanines varies in the range of 103–106 M−1 depending upon the chain length of the alkyl linkers in their structures. W. West and S. Pearce, *J. Phys. Chem.*, 69:1894–1903 (1965).

The EXAMPLES were provided to illustrate certain embodiments of the present invention and, for that reason, should not be construed in a limiting sense.

---

---

We claim:

1. An immunoassay procedure for detecting and quantifying an unknown antibody in bulk solution comprising:
   (a) placing in the bulk solution a conjugate comprising: a peptide epitope recognized by the unknown antibody, said peptide epitope having bonded thereto a pair of fluorescent materials, the peptide epitope of said conjugate capable of moving between a more folded configuration to exhibit fluorescent quenching of said conjugate and a more spaced configuration to exhibit fluorescence of said conjugate; and
   (b) adding the unknown antibody to the bulk solution to bind with the peptide epitope of said conjugate to alter the configuration of the pair of fluorescent materials from the more folded configuration to the more spaced configuration thus altering the fluorescence of said pair of fluorescent materials to detect and quantify the unknown antibody.

2. The immunoassay procedure of claim 1 wherein said flourescent materials are fluorescent energy transfer dyes.

3. The immunoassay procedure of claim 1 wherein said fluorescent materials are organic ligands of lanthanide metals.

4. An immunoassay procedure for detecting and quantifying an unknown antigen in bulk solution comprising:
   (a) placing in the bulk solution an antibody to the unknown antigen and a conjugate comprising (i) a peptide epitope recognized by said antibody, and (ii) a pair of fluorescent materials; the peptide epitope of said conjugate capable of moving between a more folded configuration to exhibit fluorescent quenching and a more spaced configuration to exhibit fluorescence when the antibody binds to the conjugate; and (b) adding the unknown antigen to the bulk solution to displace the conjugate from the antibody to alter the configuration of the pair of fluorescent materials in the conjugate from the more spaced configuration to the more folded configuration thus altering the fluorescence of the pair of fluorescent materials to detect and quantify the unknown antigen.

5. The immunoassay procedure of claim 4 wherein said flourescent materials are fluorescent energy transfer dyes.

6. The immunoassay procedure of claim 4 wherein said fluorescent materials are organic ligands of lanthanide metals.

7. An assay for detecting antibodies to a protein comprising:

providing a first peptide doubly labeled with a pair of fluorescent materials capable of moving between a more folded configuration to exhibit fluorescent quenching and a more spaced configuration to exhibit fluorescence, said first peptide capable of reacting with a first antibody directed against said protein;

introducing said first peptide into a medium which potentially contains said first antibody wherein said first peptide binds with said first antibody which alters the configuration of the first peptide pair of fluorescent materials from the more folded configuration to said spaced configuration thus altering the fluorescence of said first peptide; and detecting said fluorescence.

8. The assay of claim 7 further comprising providing a second peptide doubly labeled with a pair of fluorescent materials capable of moving between a more folded configuration to exhibit fluorescent quenching and a more spaced configuration to exhibit fluorescence, said second peptide capable of reacting with a second antibody directed against said protein, and introducing said second peptide into said medium which potentially contains said second antibody wherein said second peptide binds with said second antibody which alters the configuration of the second peptide pair of fluorescent materials from the more folded configuration to the more spaced configuration thus altering the fluorescence of said second peptide pair of fluorescent materials.

9. The assay of claim 8 wherein said first and second antibodies are directed against different epitopic regions of the same protein.

10. The assay of claim 8 wherein said flourescent materials are fluorescent energy transfer dyes.

11. The assay of claim 8 wherein said fluorescent materials are organic ligands of lanthanide metals.

* * * * *